(12) United States Patent
Higo et al.

(10) Patent No.: US 6,259,946 B1
(45) Date of Patent: Jul. 10, 2001

(54) IONTOPHORESIS DEVICE STRUCTURE

(75) Inventors: Naruhito Higo; Kazutaka Inoue; Kenji Mori, all of Ibaragi-ken (JP)

(73) Assignee: Hisamitsu Pharmaceutical Co., Ltd., Saga-Ken (JP)

( * ) Notice: Subject to any disclaimer, the term of this patent is extended or adjusted under 35 U.S.C. 154(b) by 0 days.

(21) Appl. No.: 09/331,766

(22) PCT Filed: Jan. 26, 1998

(86) PCT No.: PCT/JP98/00323

§ 371 Date: Sep. 27, 1999

§ 102(e) Date: Sep. 27, 1999

(87) PCT Pub. No.: WO98/37925

PCT Pub. Date: Sep. 3, 1998

(30) Foreign Application Priority Data

Feb. 26, 1997 (JP) .................................................... 9-060051

(51) Int. Cl.$^7$ .................................................... A61N 1/30

(52) U.S. Cl. ............................................ 604/20; 607/152

(58) Field of Search ...................... 604/20; 607/142–143, 607/149, 152–153, 115

(56) References Cited

U.S. PATENT DOCUMENTS

| | | | |
|---|---|---|---|
| 3,640,270 | * | 2/1972 | Hoffmann . |
| 3,901,218 | * | 8/1975 | Buchalter . |
| 3,942,517 | * | 3/1976 | Bowles et al. . |
| 4,014,345 | * | 3/1977 | Kameny . |
| 4,027,664 | * | 6/1977 | Heavner, Jr. et al. . |
| 4,166,453 | * | 9/1979 | McClelland . |
| 4,270,544 | * | 6/1981 | Gilden et al. . |
| 4,522,211 | * | 6/1985 | Bare et al. . |
| 4,838,273 | * | 6/1989 | Cartmell . |
| 5,221,254 | * | 6/1993 | Phipps . |

* cited by examiner

*Primary Examiner*—Mark Bockelman
(74) *Attorney, Agent, or Firm*—Sughrue, Mion, Zinn, Macpeak & Seas, PLLC

(57) ABSTRACT

It is the object of the present invention to provide an iontophoresis device structure which has excellent contouring ability at its site of attachment, has very high safety, is of high quality with high product yields, and can be produced with fewer production steps to improve working efficiency and increase productivity to allow mass production at low cost. The iontophoresis device structure of the present invention has a construction provided with a cup-shaped support including a concave part, at least one electrification hole formed in the concave part, an electrode layer laid on the flat part of the rim of the concave part, and an electrolyte layer or drug-holding layer fitted into the concave part.

12 Claims, 5 Drawing Sheets

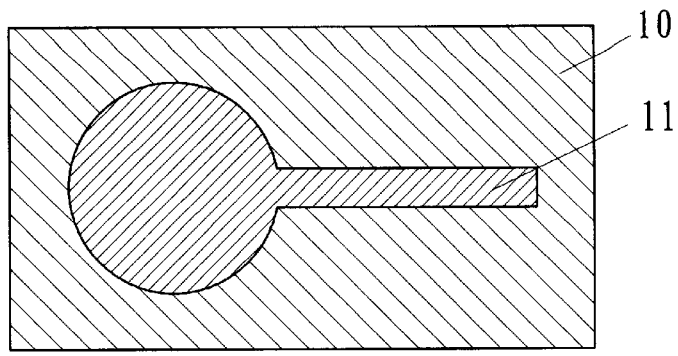
Fig. 5 (a)
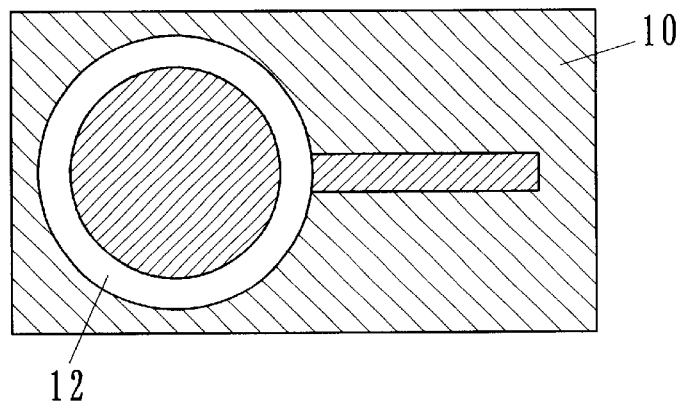
Fig. 5 (b)
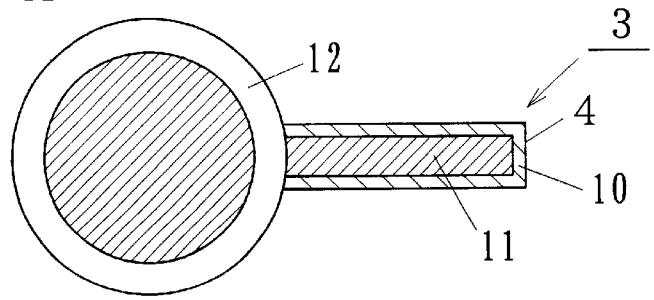
Fig. 5 (c)
Fig. 5 (d)
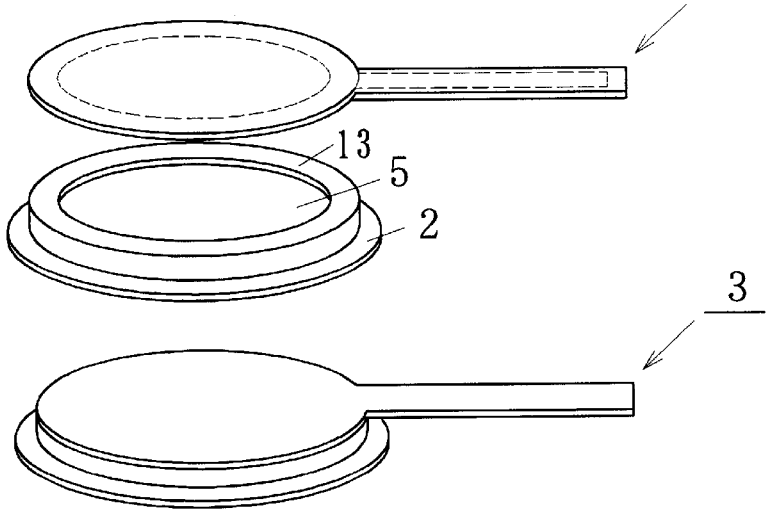
Fig. 5 (e)

Fig. 7
CONVENTIONAL
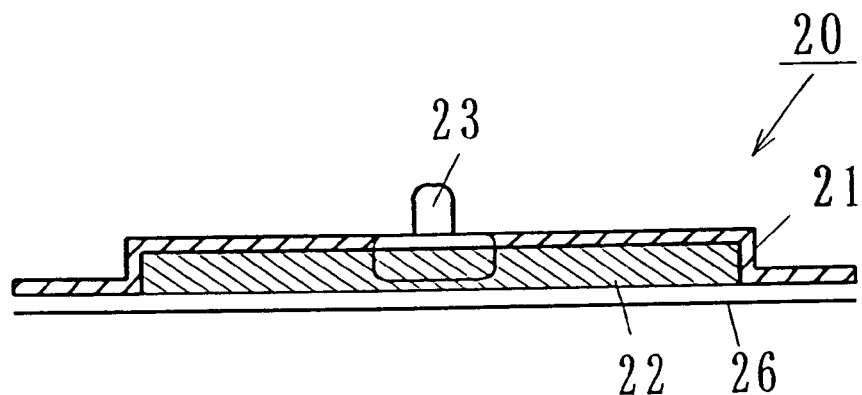
Fig. 8
CONVENTIONAL
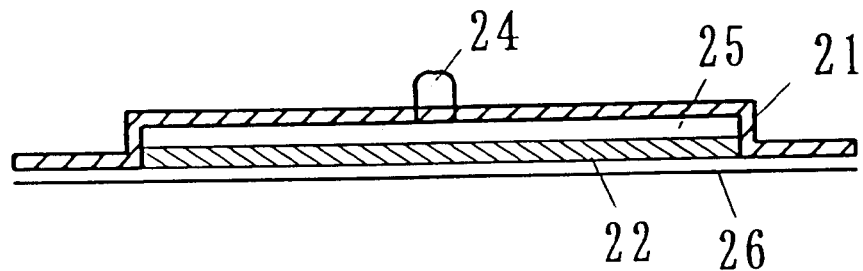

IONTOPHORESIS DEVICE STRUCTURE

TECHNICAL FIELD

The present invention relates to an iontophoresis device structure used for transdermal or transmucosal drug administration.

BACKGROUND ART

Much active research in recent years has been devoted to preparations for transdermal or transmucosal administration, because of the advantages of absorption of drugs through the skin or mucous membranes of mammals, particularly humans, as compared with oral administration, from the viewpoint of easier administration, maintenance of blood levels and the ability to avoid side effects of drugs in the alimentary tract. Iontophoresis is one area which has received much attention as an effective method for local administration which accelerates absorption of drugs through the skin or mucous membranes.

Iontophoresis is a type of method for accelerating physical absorption of drugs whereby a voltage is applied to the skin or mucous membrane to induce electrical migration of the drug, for administration of the drug through the skin or mucous membrane.

Iontophoresis apparatuses consist largely of a power source apparatus which generates a current, and an iontophoresis device structure which includes an electrode layer for attachment to the skin or mucous membrane. Normally, an iontophoresis device structure is separated into a donor electrode which includes the drug, and a reference electrode. The iontophoresis which delivers the drug through the skin or mucous membrane is accomplished by forming a single electrical circuit with the power source, the iontophoresis device structure and the body and running a current through this circuit for electrical driving.

Connection between the electrode layer of the iontophoresis device structure and the power source is achieved using a snap-type protruding terminal such as disclosed in Japanese Laid-open Patent Publication No. 504343 of 1991 or Japanese Laid-open Patent Publication No. 196644 of 1996.

A conventional iontophoresis device structure will now be explained with reference to the attached drawings.

FIG. 7 is a cross-sectional schematic view of a conventional iontophoresis device structure, and FIG. 8 is a cross-sectional schematic view of another conventional iontophoresis device structure.

Here, 20 is the conventional iontophoresis device structure, 21 is a support formed into a cup shape, 22 is an electrolyte layer fitted into the concave part of the support 21, 23 and 24 are snap-type protruding terminals, 25 is an electrode layer electrically connected to the protruding terminal 24, and 26 is a separator laminated in a freely releasable manner on the rim around the opening of the concave part of the support 21.

The method of electrification for the above-mentioned iontophoresis device structure having this construction will now be explained.

In the structure illustrated in FIG. 7, the flat section under the protruding terminal 23 is contacted with the electrolyte layer 22 for use as the electrode layer, and the protruding part is connected with an external power source for electrification.

In the structure illustrated in FIG. 8, the bottom surface of the protruding terminal 24 is contacted with a separately provided electrode layer 25 for electrical connection, and the protruding part is connected with an external electrode for electrification through the electrode layer 25 which has a wide area.

These conventional iontophoresis device structures have had the following problems, however. Specifically, (1) An insertion hole must be formed for the protruding terminal in order to project its protruding part through the bottom of the concave part of the cup-shaped support and an anchoring ring called a collar must be fitted to anchor the protruding terminal, thus requiring more working steps and reducing productivity, complicating mass production and raising costs.

(2) Leakage of the electrolyte or solvent such as water in the electrolyte layer from the insertion hole impairs the quality and lowers product yields.

(3) Because a non-flexible convex terminal is used as the snap-type protruding terminal, when the area of the underside of the terminal is widened to increase the contact between the convex terminal and the electrolyte layer in the case of the structure shown in FIG. 7, the contouring is poorer upon attachment to the body, while conversely if the underside of the terminal is reduced, a current flows directly under the lower end of the terminal, resulting in greater danger of electrical irritation to the body and lower safety.

(4) When a separate electrode layer is provided as shown in FIG. 8, it is necessary to carry out an integrating step for the more complex convex terminal as well as for the electrode layer, and thus working efficiency is reduced, productivity is impeded, and costs are increased.

(5) Although some structures employ silver or silver chloride in an ABS resin as the material for the convex terminal, and other structures have nickel platings on zinc, when ABS resins are used the terminal must be formed to a prescribed thickness to provide strength for the convex terminal, and hence there is a limit to how thin the thickness of the lower end of the terminal can be made. Also, structures wherein zinc is covered with a nickel plating, etc., have the problem of elution of the zinc or nickel, etc., by the electrolyte reaction upon electrification, so that the safety is poorer.

(6) When the protruding terminal is connected with the external power source, excessive pressure on the protruding terminal may break the iontophoresis device structure and cause leakage of its contents, such as the electrolyte layer.

(7) Because the rim of the protruding terminal is round, the connector is prone to detachment during electrification by the external power source.

The present invention overcomes these problems by providing an iontophoresis device structure which has excellent contouring ability at its site of attachment, has very high safety, is of high quality with high product yields, and can be produced with fewer production steps to improve working efficiency and increase productivity to allow mass production at low cost.

DISCLOSURE OF THE INVENTION

In order to achieve the object stated above, the present invention has the following construction.

The iontophoresis device structure according to claim 1 of the invention has a construction provided with a cup-shaped support including a concave part, at least one electrification hole formed in the concave part, an electrode layer formed on the flat part of the rim of the concave part, and an electrolyte layer fitted into the concave part.

Since the electrode layer is anchored on the outside of the flat part of the rim around the concave part of the support in this construction, its production is more simple allowing notable improvement in working efficiency, increasing productivity and lowering the cost. In addition, the adhesion between the flat part of the rim and the electrode layer around the concave part can be markedly increased, to help prevent leakage of the solvent of the electrolyte layer, etc.

Here, the support serves to hold the electrolyte layer, and it may be any material with excellent workability, flexibility and suitable shape retention and water retention; as examples there may be mentioned chlorinated resins such as vinylidene chloride and vinyl chloride polymers, as well as olefin-based, ester-based, styrene-based, acrylic-based, amide-based, oxymethylene-based, phenylene sulfide-based, amidoimide-based, acrylonitrile-based, etherketone, ethersulfone, sulfone, etherimide, butadiene and isoprene high molecular polymers or their copolymers, though there is no restriction to these and it is only necessary that the material have the effect mentioned above. Materials which have been formed into films and worked, or molded products, may be used. The thickness is not particularly restricted, but a thickness of 5–250 $\mu$m is preferred for superior shape retention and flexibility.

The electrolyte layer is a conductive layer containing an electrolyte which supplies the body with a current from the power source when directly contacted with human skin or a mucous membrane, and it is preferred to use a nonwoven fabric impregnated with an electrolyte solution, or an electrolyte solution which has been gelled with a polysaccharide such as agar or gelled using a synthetic polymer.

The iontophoresis device structure according to claim 2 of the invention has the construction of claim 1 wherein the electrode layer is provided with an electrode layer base formed of a film or sheet of a thermoplastic synthetic resin, and a conductive layer formed on one side of the electrode layer base.

In this construction, the flexible electrode layer matches the soft support and can therefore follow the shape of the site of attachment. Also, since the electrode layer is made of an easily moldable synthetic resin, the number of production steps can be reduced to increase productivity.

The electrode layer base is a base sheet with a conductive layer on the bottom side, and its shape is not limited to circular but may be elliptical, square or rectangular; the electrode terminal may likewise have any desired shape, and if necessary a connector-anchoring cavity may be formed in the terminal for more stable anchoring with the connector, etc.

The material used for the electrode layer base may be the same material as the support. It is preferred to use an identical synthetic resin as the support in order to allow intimate heat sealing. Different types of synthetic resins may also be used depending on the position and material of the conductive layer.

The material used for the conductive layer may be metal foil, carbon foil or the like, but preferably a conductive ink paste is directly printed on a polymer sheet. As examples of such conductive ink paste materials there may be mentioned polarized electrode materials such as resin paints comprising mixtures of carbon powder or graphite powder, non-polarized materials such as silver- or copper-based materials for the anode and resin materials comprising silver/silver chloride, copper/copper chloride mixtures for the cathode; however, non-polarized materials which do not produce foaming under pH changes or electrolysis of water are particularly preferred for use.

The iontophoresis device structure according to claim 3 of the invention has the construction of claim 1 or 2 wherein the electrode layer is laid onto the flat part via an adhesive layer.

According to this construction, the electrode layer may be anchored to the surface of the flat part by simple adhesion with an adhesive agent, and since it is adhered on the outside of the support it is possible to prevent coating leakage of the adhesive agent and ensure anchorage of the electrode layer. Because the electrode layer and the cup-shaped support are thoroughly bonded, leakage and escape of the contents can be reliably prevented. The flexibility of the structure as a whole provides a better feel during use and makes it easier to design a line for mass production.

The iontophoresis device structure according to claim 4 of the invention has the construction of claim 3 wherein the adhesive agent of the adhesive layer is of one or more types from among acrylic-based, silicon-based or rubber-based pressure sensitive adhesive agents and heat sealing agents such as polyolefins or their esters.

According to this construction, the adhesive agent used is one which is commonly used, such as a pressure-sensitive adhesive agent which is an acrylic-based agent with high adhesive strength, a silicon-based agent which is resistant to corrosion in gel contents or an inexpensive rubber-based agent, or a heat sealing agent made of a polyolefin or its ester. These may be appropriately selected depending on the size and the purpose of use of the iontophoresis device structure. The adhesive agent accomplishes thorough sealing between the electrode layer and the flat part of the support, for a tight sealing effect.

When heat sealing is carried out for adhesion between the electrode layer and the cup, the heat sealing temperature will depend on the melting point of the aforementioned polymer film, but will generally be 100–250° C., and preferably 120–200° C. As the heat sealing temperature increases above 200° C., cracks will tend to be produced in the electrode layer, while as it decreases below 120° C. more time will be required for the heat sealing, which will tend to lower working efficiency, and therefore neither extreme is preferred.

The iontophoresis device structure according to claim 5 of the invention has the construction according to any one of claims 1 through 4, wherein the electrode layer has an electrification connecting member from the external power source, and the connecting member is a projection formed as a bulge from the rim of the electrode layer, or a recess formed parallel to the direction of height of the rim of the concave part of the support and the exposed part of the electrode layer which is exposed at the recess.

According to this construction, connection with the external power source for administration of the preparation can be simplified because of the projection provided.

Here, the size of the projection or exposed electrode layer as the connecting member may be a sufficient size or length to allow electrical connection with different types of connectors, and in order to prevent misconnection with the connector, a connector latch with a thickened end may be provided. A connection hole for the connector may also be opened in the projection or exposed electrode layer.

BRIEF DESCRIPTION OF THE DRAWINGS

FIGS. 5(a)–5(e) are series of sketches showing the production steps for the iontophoresis device structure according to the first embodiment of the invention.

FIG. 7 is a cross-sectional schematic view of a conventional iontophoresis device structure.

FIG. 8 is a cross-sectional schematic view of another conventional iontophoresis device structure.

BEST MODE FOR CARRYING OUT THE INVENTION

Embodiments of the present invention will now be explained with reference to the drawings.

First Embodiment

Figure 1:
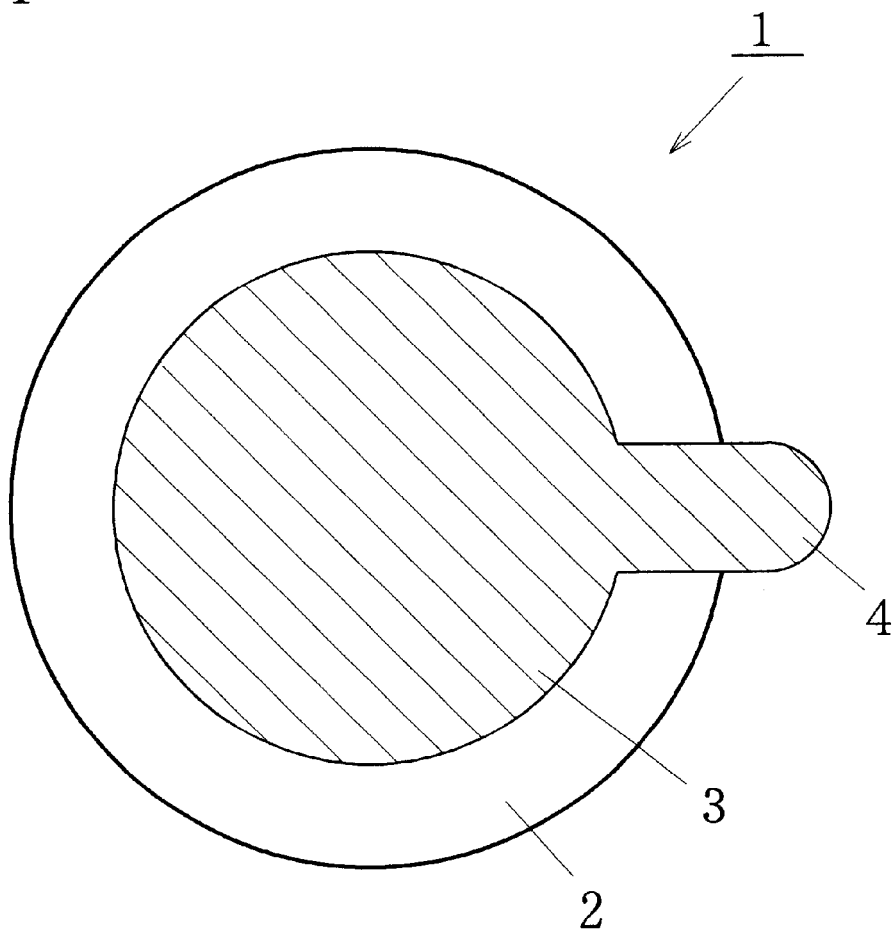
FIG. 1 is a plan view of an iontophoresis device structure according to a first embodiment of the invention.
Figure 2:
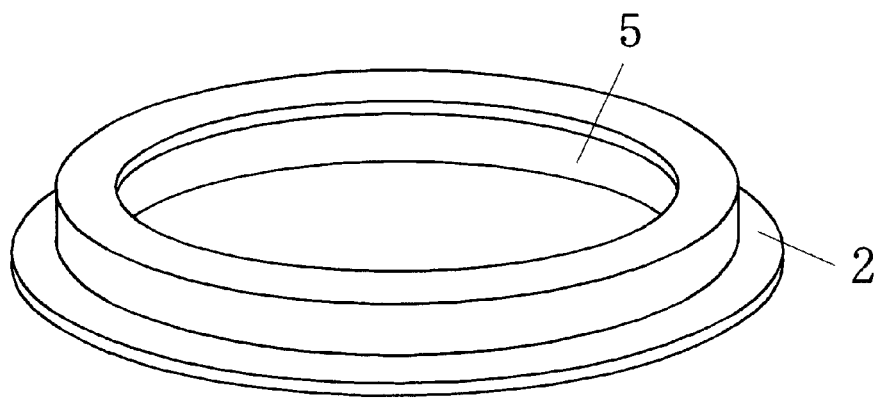
FIG. 2 is a perspective view of the support of an iontophoresis device structure according to the first embodiment of the invention.
Figure 3:
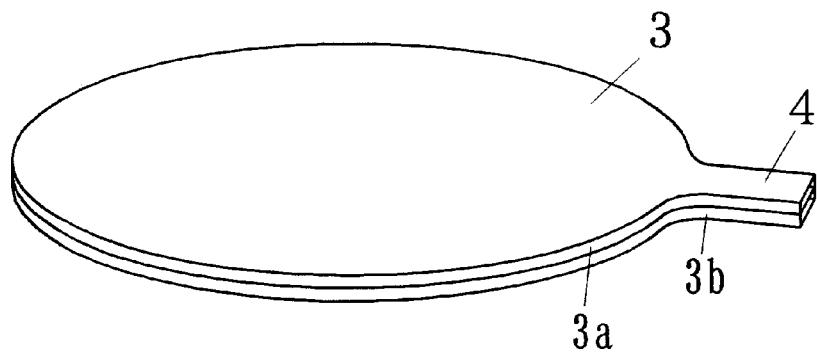
FIG. 3 is a perspective view of the electrode layer of the iontophoresis device structure according to the first embodiment of the invention.
Figure 4:
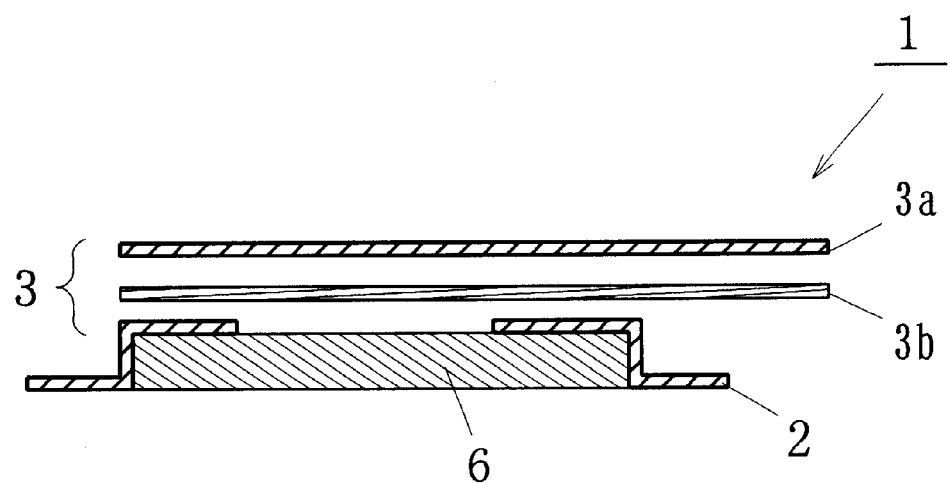
FIG. 4 is a cross-sectional view showing major parts of the assembly of the iontophoresis device structure according to the first embodiment of the invention.

FIG. 1 is a plan view of an iontophoresis device structure according to the first embodiment of the invention, FIG. 2 is a perspective view of its support, FIG. 3 is a perspective view of its electrode layer and FIG. 4 is a cross-sectional view showing major parts of its assembly.

In FIGS. 1 and 2, 1 is the iontophoresis device structure according to this embodiment, 2 is the support formed into a cup shape from a thermoplastic resin such as polyethylene terephthalate, 3 is the electrode layer, 4 is the projection formed as a partial extension of the electrode layer 3, and 5 is an electrification hole formed as a single opening in the bottom of the concave part of the support 2. In FIG. 3, the electrode layer 3 is formed of an electrode layer base 3a and a conductive layer 3b, the electrode layer base 3a being formed of a polyethylene terephthalate film and the conductive layer 3b being formed by printing of conductive silver paste ink (product name: Achison ED6022 by Nihon Achison) on the surface of the electrode layer base 3a to a dry thickness of about 20 μm. In FIG. 4, 6 is an electrolyte layer made of a gel or the like packed into the concave part of the support 2.

The support 2 here is formed into a circular shape, but it may also be elliptical or rectangular. Also, only one electrification hole 5 was formed in the support 2, but 2 or more holes, or a mesh, may also be formed.

A process for fabricating the iontophoresis device structure of this embodiment having the construction described above will now be explained with reference to the drawings.

FIG. 5 is a series of sketches showing the production steps for the iontophoresis device structure of this embodiment.

In the drawings, 10 is an electrode layer base-forming material made of a polyethylene terephthalate or other thermoplastic synthetic resin film or sheet with a thickness of 100 μm, 11 is a conductive layer formed by printing of conductive silver paste ink (product name: Achison ED6022 by Nihon Achison) on the electrode layer base-forming material 10 to a dry thickness of about 20 μm, 12 is an adhesive layer made of a heat sealing agent or pressure sensitive adhesive agent applied around the rim of the conductive layer 11, and 13 is the flat part of the support 2.

The fabrication process involves first printing the silver paste ink on the electrode layer base-forming material 10 as shown in (a) to form the conductive layer 11 (conductive layer-forming step), and then coating the rim of the conductive layer 11 with a heat sealing agent or pressure sensitive adhesive agent to about the same width as the flat part 13 of the support 2 as shown in (b), to make the adhesive layer 12 (adhesive layer-forming step). Next, the electrode layer base-forming material 10 is cut out leaving the electrode layer 3 and a projection 4 as shown in (c) (cutting step). The adhesive layer 12 is then laid onto the flat part 13 of the separately formed support 2 as shown in (d) and heat sealed to obtain the iontophoresis device structure.

Second Embodiment

Figure 6:
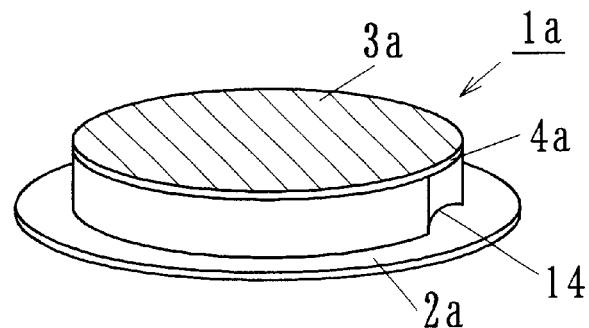
FIG. 6(a) is a perspective view of an iontophoresis device structure according to a second embodiment of the invention.
FIG. 6(b) is a plan view of the iontophoresis device structure according to the second embodiment of the invention.
FIG. 6(c) is a plan view of the support of the iontophoresis device structure according to the second embodiment of the invention.
Figure 6:
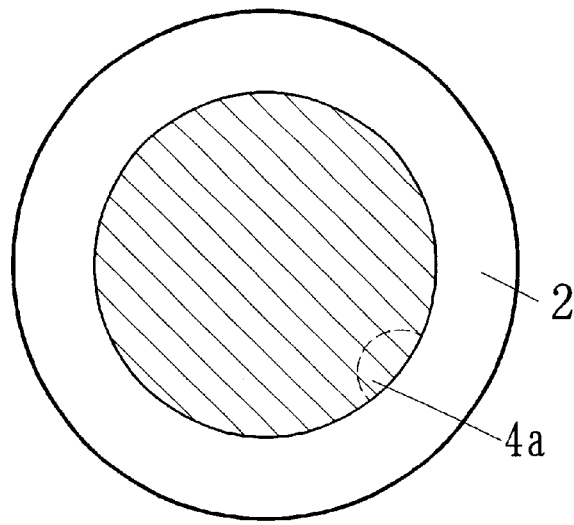
Figure 6:
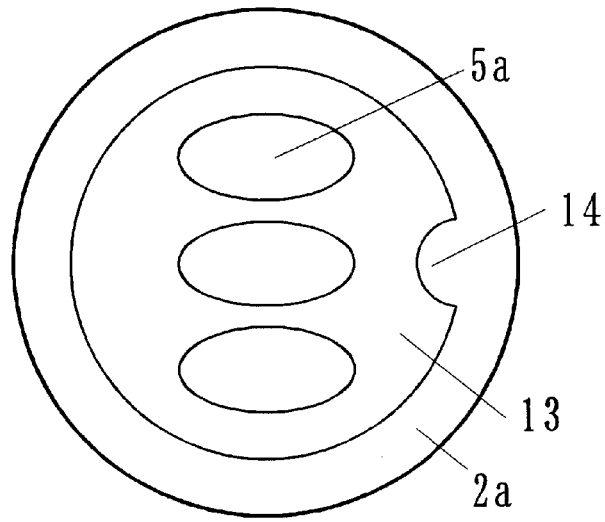

FIG. 6(a) is a perspective view of an iontophoresis device structure according to a second embodiment of the invention, FIG. 6(b) is a plan view thereof, and FIG. 6(c) is a plan view of its support.

In the drawings, 1a is the iontophoresis device structure of the second embodiment, 2a is the support, 3a is the electrode layer formed into a circle, 4a is the exposed electrode layer as one of the connecting members, 5a indicates electrification holes formed at 3 locations on the flat part 13, and 14 is a recess formed parallel to the direction of height of the concave part of the support 2a.

According to this embodiment, the recess 14 under the exposed electrode layer 4a allows easier connection with a connector. An additional effect is that if a separator is sealed to the support after the electrolyte layer or other contents have been packed into the concave part, sealing is thus facilitated since no protruding projection is present.

Industrial Applicability

As explained above, the present invention makes it possible to realize an iontophoresis device structure which provides the following excellent effects.

(a) escape and leakage of the contents can be reliably prevented by simple attachment of the electrode layer to the cup-shaped support which holds the electrolyte, to obtain a very high quality iontophoresis device structure.

(b) because the entire structure is flexible, it easily follows the shape of the site of attachment, so that it may be attached without causing discomfort.

(c) since very few production steps are necessary, mass production is possible at low cost.

(d) the connecting member allows connection with a power source to be accomplished very easily and reliably.

(e) Since no hard protruding terminal is present, it is easy to house the structure during transport and storage.

What is claimed is:

1. An iontophoresis device structure, characterized by being provided with a cup-shaped support including a concave part, at least one electrification hole formed in said concave part, an electrode layer laid on the flat part of the top outer rim of said concave part, and an electrolyte layer fitted into said concave part; and said electrode layer is provided with an electrode layer base formed of a film or sheet of a thermoplastic synthetic resin, and a conductive layer formed on one side of said electrode layer base facing the electrification hole.

2. An iontophoresis device structure according to claim 1, characterized in that said electrode layer is provided with an electrode layer base formed of a film or sheet of a thermoplastic synthetic resin, and a conductive layer formed on one side of said electrode layer base.

3. An iontophoresis device structure according to claim 2, characterized in that said electrode layer is laid onto said flat part via an adhesive layer.

4. An iontophoresis device structure according to claim 6, characterized in that the adhesive agent of said adhesive layer is of one or more types from among acrylic-based, silicon-based or rubber-based pressure sensitive adhesive agents and heat sealing agents such as polyolefins or their esters.

5. An iontophoresis device structure according to claim 4, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

6. An iontophoresis device structure according to claim 3, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

7. An iontophoresis device structure according to claim 2, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

8. An iontophoresis device structure according to claim 1, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

9. An iontophoresis device structure according to claim 1, characterized in that said electrode layer is laid onto said flat part via an adhesive layer.

10. An iontophoresis device structure according to claim 3, characterized in that the adhesive agent of said adhesive layer is of one or more types from among acrylic-based, silicon-based or rubber-based pressure sensitive adhesive agents and heat sealing agents such as polyolefins or their esters.

11. An iontophoresis device structure according to claim 10, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

12. An iontophoresis device structure according to claim 9, characterized in that said electrode layer has an electrification connecting member from the external power source, and said connecting member is a projection formed as a bulge from the rim of said electrode layer, or a recess formed parallel to the direction of height of the rim of said concave part of said support and the exposed part of said electrode layer which is exposed at said recess.

* * * * *